United States Patent [19]

Butler et al.

[11] Patent Number: 4,941,879
[45] Date of Patent: Jul. 17, 1990

[54] SINGLE USE SYRINGE

[75] Inventors: John H. A. Butler, 3 St. Mervyns Avenue, Double Bay, New South Wales 2028; Sandy Richardson, Double Bay, both of Australia

[73] Assignee: John H. A. Butler, Double Bay, Australia

[21] Appl. No.: 373,291
[22] PCT Filed: Oct. 14, 1988
[86] PCT No.: PCT/AU88/00402
§ 371 Date: Jul. 10, 1989
§ 102(e) Date: Jul. 10, 1989
[87] PCT Pub. No.: WO89/03698
PCT Pub. Date: May 5, 1989

[30] Foreign Application Priority Data

Oct. 14, 1987 [AU] Australia .................................. PI4881
Mar. 29, 1988 [AU] Australia .................................. PI7493
Jul. 29, 1988 [AU] Australia .................................. PI9554
Sep. 13, 1988 [AU] Australia .................................. PJ0376

[51] Int. Cl.⁵ .............................................. A61M 5/00
[52] U.S. Cl. ..................................... 604/110; 604/236
[58] Field of Search ............... 604/110, 187, 236, 237, 604/238, 246, 247, 249, 207

[56] References Cited

U.S. PATENT DOCUMENTS 4,233,975 11/1980 Yerman ............................... 604/110
4,643,723 2/1987 Smit ..................................... 604/236
4,781,683 11/1988 Wozniak et al. .................. 604/236 x Primary Examiner—John D. Yasko
Attorney, Agent, or Firm—Christopher J. Rudy

[57] ABSTRACT

A single use syringe having an interacting piston and cylinder which cooperate to define a variable volume working space, the syringe includes a valve body located in the chamber so as to divide the chamber into a first and second sub-chamber, the valve body has valves which permit a liquid to be initially drawn into the syringe and then injected, but prevent a subsequent liquid being drawn into the syringe.

7 Claims, 11 Drawing Sheets

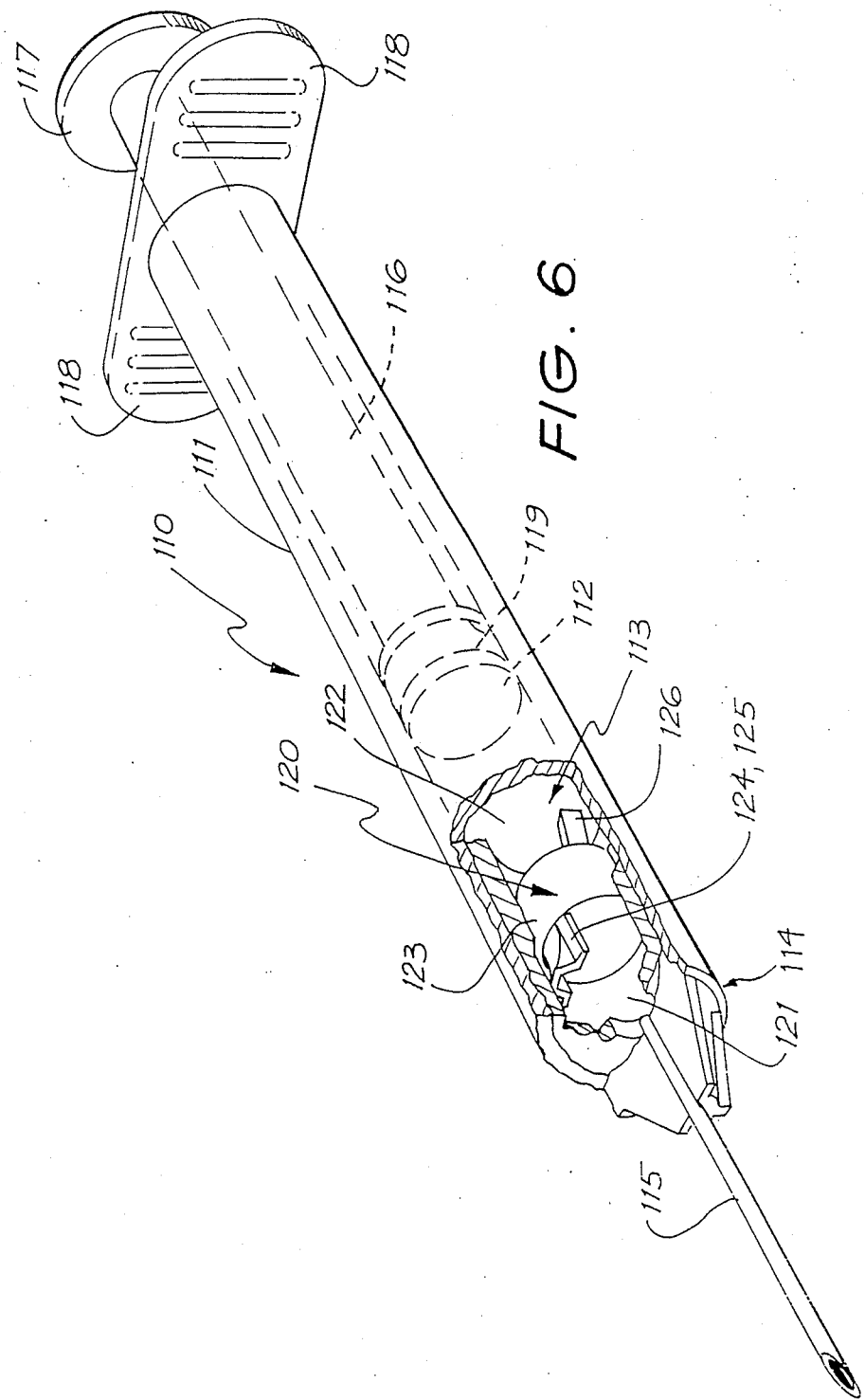

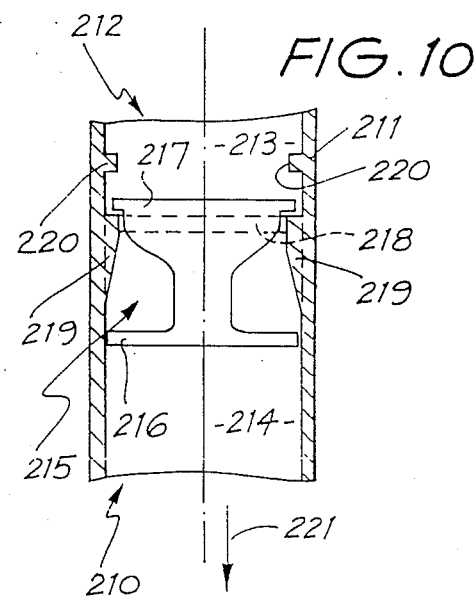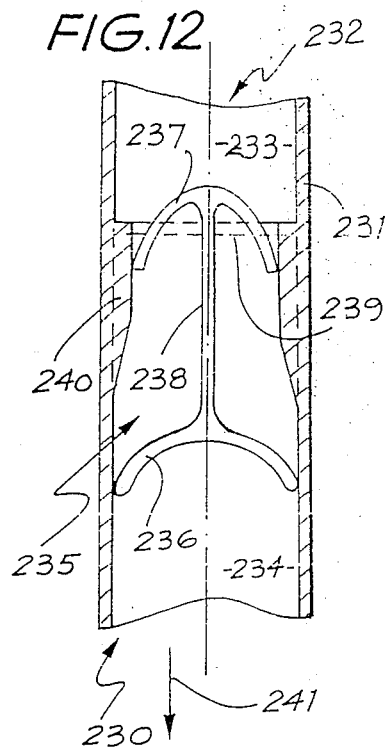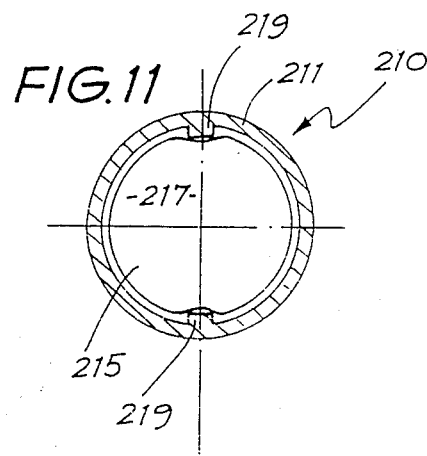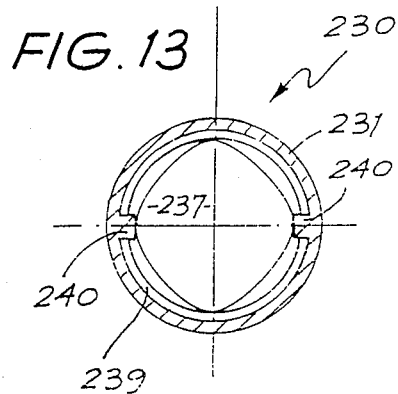

SINGLE USE SYRINGE

The invention relates to hypodermic syringes and in particular to a single use hypodermic syringe Disposable syringes for which a single use is contemplated are well known as for example syringes for the injection of insulin in diabetics. Nothing, however, prevents these syringes from being reused in a necessarily unsterile state. The result that contamination syringes when used contribute to the spreading of disease such as AIDS or hepatitis.

Accordingly is desirable for syringes to be designed for a single use only to inhibit their re-use and therefore the risk of using contaminated syringes.

Previously known single use syringes usually incorporate a modification of the piston of the syringe so that it is jammed in its fully inserted position adjacent the needle. These previously known devices have the disadvantage that the piston can become inadvertently jammed prior to a liquid being drawn into the cylinder of the syringe.

Described in British Patent No. 1,550,310 and French Patent No. 2,348,708 is a single use syringe. The syringe has a detachable piston which prevents re-use of the syringe. Once the piston has been moved to the minimum volume position, movement of the piston to again draw in a liquid is prohibited since the piston rod becomes detached from the piston head. This syringe suffers from the disadvantage that the piston can become detached from the piston rod and the syringe cannot be operated to test whether the syringe has been correctly inserted. This is usually achieved by pulling back on the piston rod to draw into the syringe a small portion of blood. A similar syringe is disclosed in British Patent No. 2,015,883 again this particular device shows a detachable piston which suffers from the disadvantages as discussed.

French Patent No. 2,298,340 discloses a single use syringe, with the piston being provided with a frangible diaphragm. Once the piston has been moved to the minimum volume position, a bar penetrates the diaphragm preventing re-use of the syringe. British Patent No. 1,454,540 is of a similar construction, in that the piston is provided with a means of damaging the body of the syringe preventing its re-use. Both the syringes suffer from the disadvantage that they do not enable operation of the syringe to test whether the needle has be correctly located.

U.S. Pat. No. 3,951,146 discloses a single use syringe which employs a ratchet mechanism to prevent withdrawal of the piston. Again this particular type of syringe does not enable testing to determine whether the needle has been correctly located British Patent No. 2,184,657 also uses a pawl to engage behind the piston to prevent re-use. It has the same disadvantages. U.S. Pat. Nos. 3,478,937 and 3,890,971 also employ pawls or detent members which prevent reward movement of the piston. They suffer similar disadvantages.

U.S. Pat. No. 4,233,975 discloses a single use syringe with a plunger member which engages within a socket when the piston is moved to the minimum volume position. The plunger cannot be retracted and prevents re-use of the syringe.

U.S. Pat. No. 4,650,468 is similar to several of the above discussed patents since it also uses a plunger or piston which is automatically locked in a position preventing re-use.

The above discussed previously known single use syringes suffer from the further disadvantage in that they require the piston to be moved to the minimum volume of position before any action is taken to render the syringe inoperative.

It is the object of the present invention to overcome or substantially ameliorate the above disadvantages.

There is disclosed herein a single use syringe comprising:

an inter-acting piston and cylinder defining a variable volume chamber within which a liquid to be injected is drawn;

a needle mounting at one end of said cylinder, to receive a needle, a passage extending through said mounting enabling liquid communication between said cylinder and said needle;

a piston rod attached to said piston and operable by a user to cause movement of said piston to vary the volume of said chamber;

a valve means including a valve body located within said chamber between said mounting and said piston and dividing said chamber into a first sub-chamber located between said mounting and valve means, and a second sub-chamber located between said valve means and said piston, said valve body being movable longitudinally of said cylinder between a first position and a second position, and said valve means includes a first valve which, when said body is in said first position, permits flow from said first sub-chamber to said second sub-chamber and prevents flow from said second sub-chamber to said first sub-chamber, but when said body is in said second position, said first valve permits flow from said second sub-chamber to said first sub-chamber and prevents flow from said first sub-chamber to said second sub-chamber, and a second valve which, when said body is in said first position, permits flow from said first sub-chamber to said second sub-chamber, but prevents flow from said first sub-chamber to said second sub-chamber when said body is in said second position; and means to prevent movement of said body from said second position to said first position.

There is further disclosed herein a valve assembly for a syringe having an interacting piston and cylinder, with the cylinder terminating at one end with a mounting to receive a syringe needle, said piston and cylinder co-operating to define a variable volume working chamber which receives a liquid to be injected by the syringe, said valve assembly being adapted to be located within said chamber so as to divide said chamber into a first sub-chamber located adjacent the needle mounting, and a second sub-chamber located adjacent the piston, said valve assembly including a valve sleeve to be sealingly received within said cylinder so as to be coaxial with respect thereto, said sleeve having an internal peripheral surface;

a movable valve member received within said sleeve and sealingly co-operating therewith so that in use of the syringe the valve member selectively controls the direction of flow of liquid within the syringe, said valve member having a pair of axially spaced annular sealing surfaces which sealingly engage said sleeve, and which are resiliently deformable;

a first set of sleeve projections extending inwardly of said sleeve to engage a first one of said sealing surfaces;

a second set of sleeve projections extending inwardly of said sleeve to engage the other sealing surface, said second set of sleeve projections being spaced longitudinally of said first set of sleeve projections; and wherein said valve member is longitudinally movable between a first portion wherein the first annular sealing surface is engaged with the first set of sleeve projections so as to be deformed and deflected from said sleeve so that liquid may pass thereby, and the other sealing surface is in sealing contact with said sleeve and inhibits the direction of fluid flow in a first direction, and a second position wherein said second sealing surface is engaged with said second set of sleeve projections so that liquid may pass thereby, and said first sealing surface is sealingly engaged with said sleeve to inhibit fluid flow in a second direction, which is opposite to said first direction.

A preferred form of the present invention will now be described by way of example with reference to accompanying drawings, wherein:

FIG. 6 is a schematic part sectioned perspective view of a single use syringe;

FIG. 10 is a schematic sectioned side elevation of a portion of a syringe;

FIG. 11 is a schematic end elevation of the portion of FIG. 10;

FIG. 12 is a schematic side elevation of a further syringe portion;

FIG. 13 is a schematic end elevation of the portion of FIG. 12;

Figure 1:
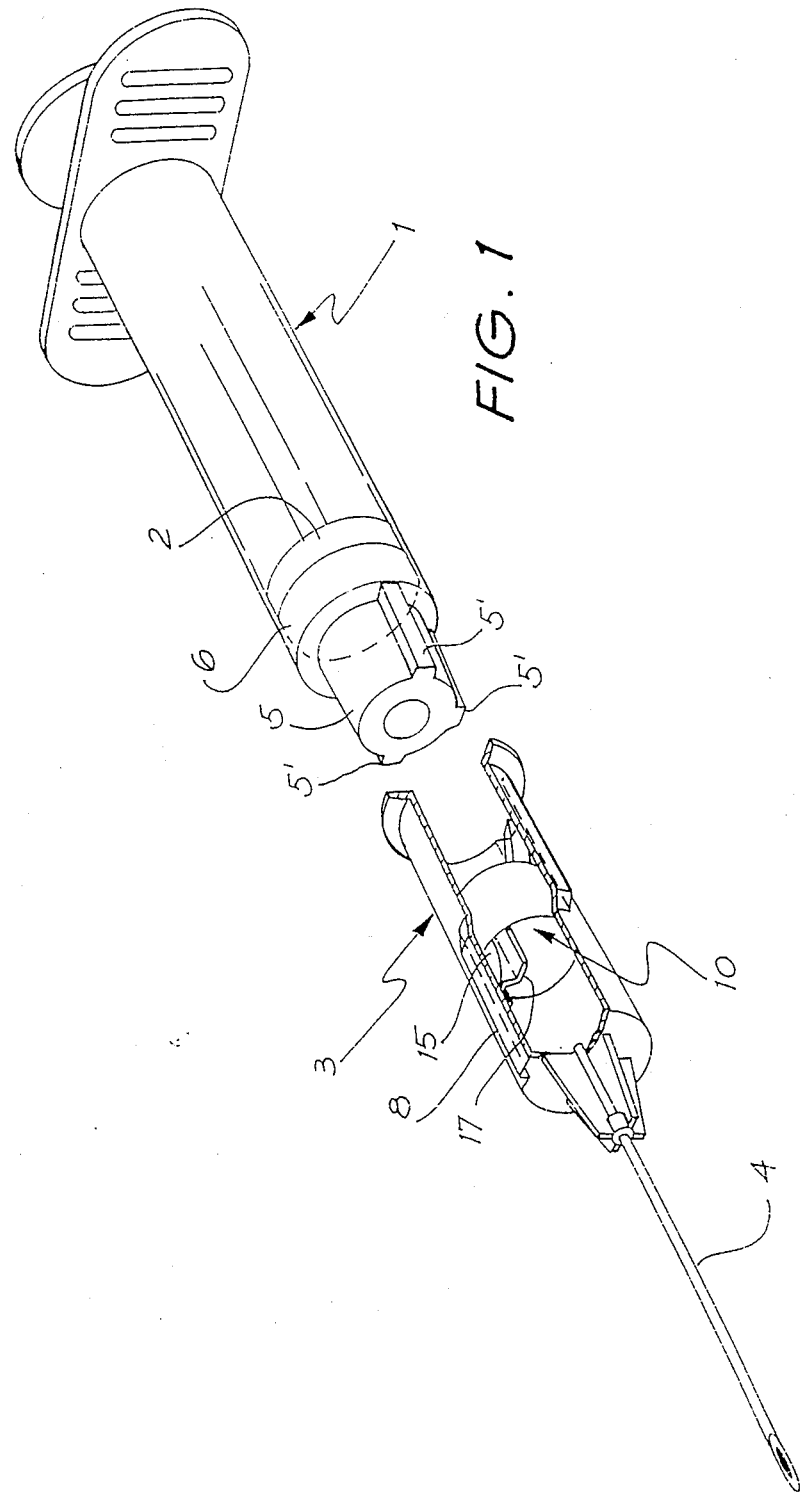
FIG. 1 is a schematic perspective part section view of a single use syringe.

In the preferred embodiment of the invention shown in the FIGS. 1 to 5, the valve has been incorporated in the needle portion 3 of a syringe, the syringe main body portion 1 and needle portion 3 being made preferably as separate pieces. The valve includes a sliding portion 10 comprising a cylindrical body 14, at the opposite ends of which peripheral seals 34 and 36 are provided. Flexible flaps 17 and 19 extend from opposite ends and at diametrically opposed sections from arms 15 and 16 of cylindrical body 14. In co-operation with the wall 13 of the syringe flap 19 acts as an inlet valve while the flap 17 acts as an outlet valve in a manner to be described below.

The wall 13 includes two outwardly extending portions 8 and 9. Portion 8 has a sloping portion extending from point 24 to point 32 to provide channel 18. The portion 9 has a sloping portion from point 22 to point 23 to provide channel 21. The wall 13 is also provided with a portion 28 extending towards the needle 4 from point 22, ending in a shoulder 25 which forms a stop for the body 14 in a manner to be explained below.

Figure 2:
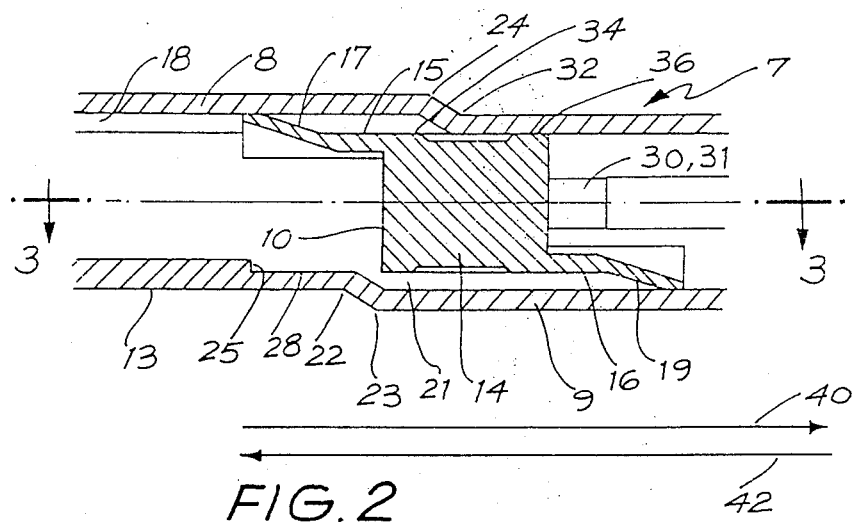
FIG. 2 is a schematic section side elevation of a portion of the syringe of FIG. 1 in a first operative mode.

The flaps 17 and 19 are made of such a resilient material that in their resting state as shown in FIG. 2 they lie against the wall 13. The flaps 17 and 19 as shown in FIGS. 1. 2 and 4 are shaped so as to provide a sealing action not only against wall 13 within channels 18 and 21 but also against the side walls of these channels.

Figure 3:
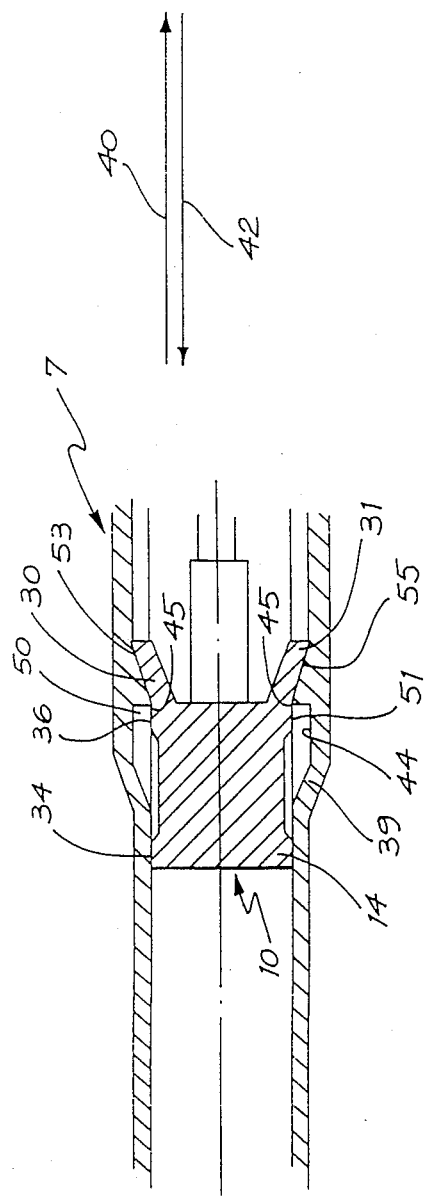
FIG. 3 is a schematic sectioned side elevation of the syringe portion of FIG. 2.

At approximately right angles to the flaps 17 and 19 a pair of fingers 30 and 31 is provided as best shown in FIG. 3. These fingers extend from the body 14 near seal means 36 and at the end of sliding portion 10 distal of the needle tip 4. Fingers 30 and 31 extend into channels 50 and 51, which are interrupted by inclined surfaces 53 and 55 which lead to forwardly facing shoulders 45. The fingers 30 and 31 are suitably resilient to enable them to bend upon motion of the sliding portion 10 in the forward direction of arrow 42 so that upon passing the shoulder 45 they re-enter the channels 50 and 51 and thereby prevent return movement of the valve body 10. In addition, the fingers 30 and 31 help to centre the body 10 within the wall 13, for example, by seating against the inclined surfaces 53 and in their initial state.

The operation of the valve will now be described with particular reference to FIGS. 2, 3 and 4. The drawing of fluid into the needle 4 in the direction of arrow 40 will cause the flap 19 to move away from the wall in the channel 21, allowing fluid past the cylindrical body 14 via channel 21. The flap 19 will remain open as long as the filing stroke continues.

Once the desired dose has been drawn up the plunger 2 is moved in the direction of arrow 42. This initiates an expulsion stroke. The pressure of fluid being forced in the direction of arrow 42 by the plunger 2 in the main body portion 1 of the syringe causes the flap 19 to seat against the surface of the fixed portion 13. The cylindrical part 14 is driven in the direction of arrow 42 by fluid pressure. This forces the seal 34 of the body 14 against point 22 to completely close channel 21 while dragging flap 19 therealong. Further motion in the direction of arrow 42 can continue until the body 14 presses against should 25 to be stopped thereby (FIG. 4).

Once the seal 36 of the cylindrical part 14 has cleared the point 32 fluid pressure will open the flap 17 to allow expulsion of fluid through the needle top portion 4. Concurrently the fingers 30 and 31 become engaged forward of the shoulders 45. The expulsion stroke of the syringe is completed as desired.

Refilling of the syringe is now prevented. Flap will allow expulsion of the contents of a syringe but upon initiation of a stroke in the direction of arrow 40 the flap 17 will engage the wall 13 preventing the filling of the syringe, while the body 14 moves slightly in the direction of arrow 40 until engagement of the fingers 30 and 31 with the shoulders 45 prevents further movement of the body 14. The body 14 is then then located with the seal 36 in contact with the wall 13 at point 32 so that the flow of fluid in the direction of arrow 40 is prevented. This effectively limits the syringe having these valve means to being used for single filling and expulsion stroke.

The material used for the body 14, the flaps 17, 19 and the fingers 30 and 31 may be any suitably resilient and pharmacologically acceptable material such as nonprene.

Figure 5:
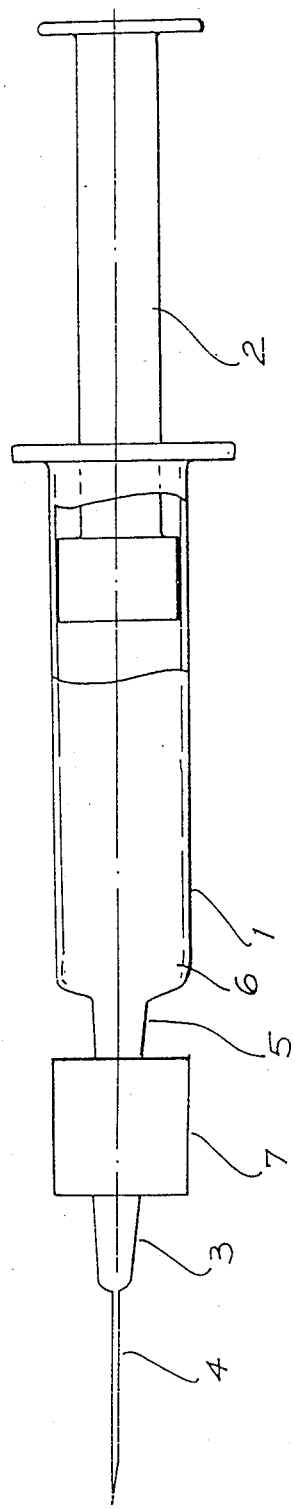
FIG. 5 is a schematic side elevation of an alternative syringe to that shown in FIG. 1.
Figure 9:
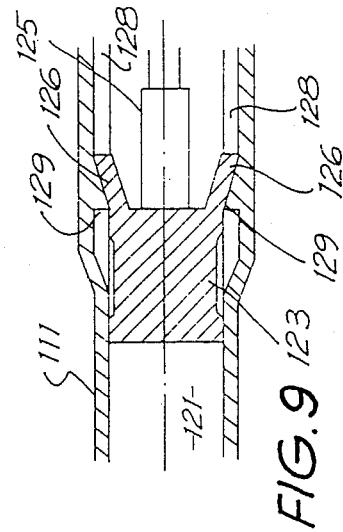
FIG. 9 is a schematic sectioned side elevation of the portion of FIG. 7 sectioned along the line 9—9.
Figure 7:
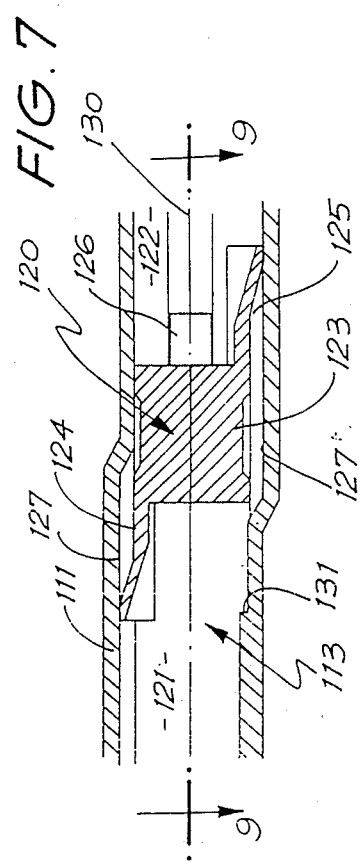
FIG. 7 is a schematic sectioned side elevation of a portion of the syringe of FIG. 6, with the syringe in a first mode of operation.
Figure 8:
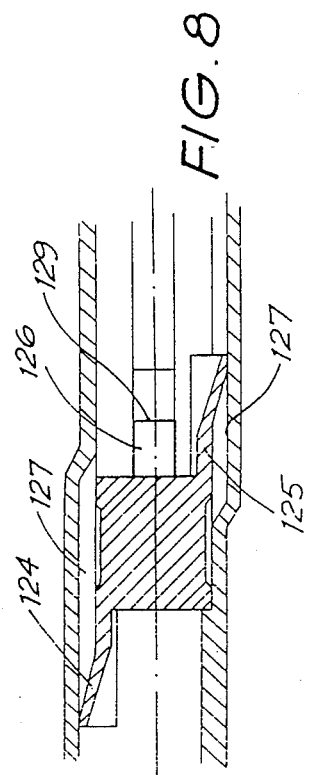
FIG. 8 is a schematic sectioned side elevation of the portion of FIG. 7 with the syringe in a second mode of operation.
Figure 14:
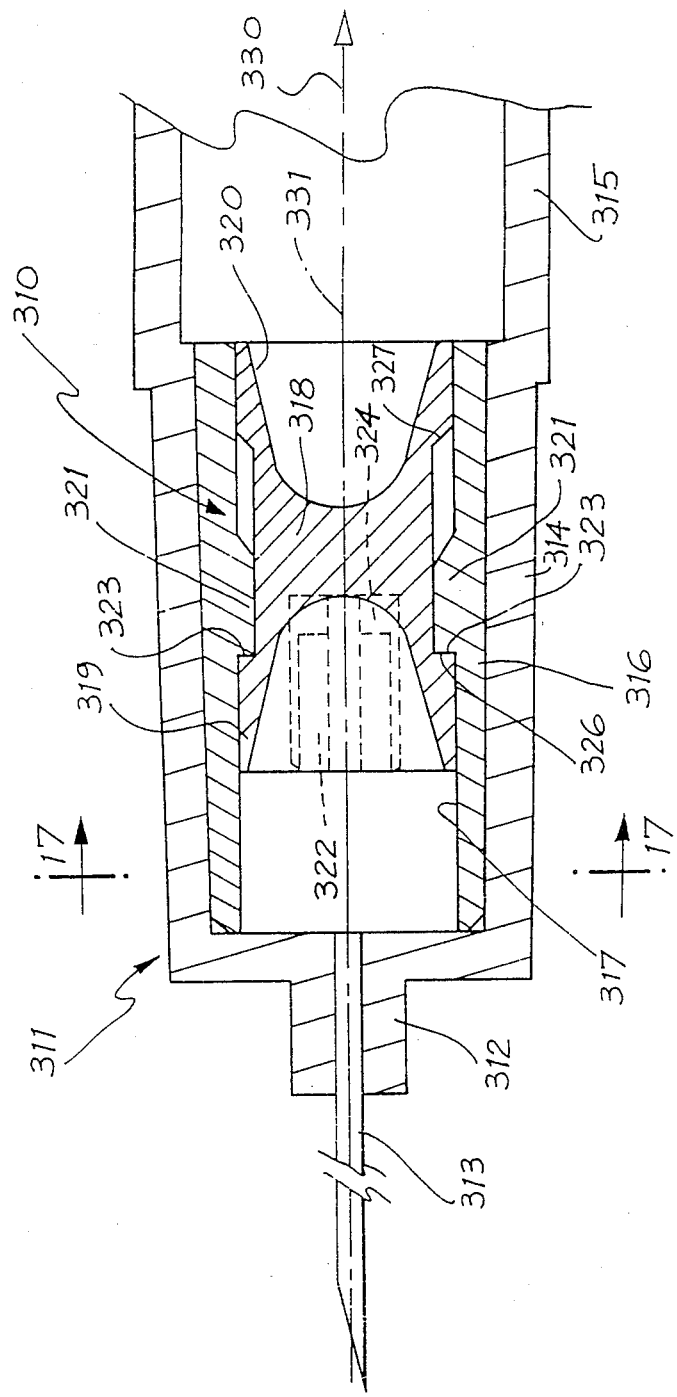
FIG. 14 is a schematic part sectioned side elevation of a valve assembly of a single use syringe, with the valve member thereof in a first operative position.
Figure 15:
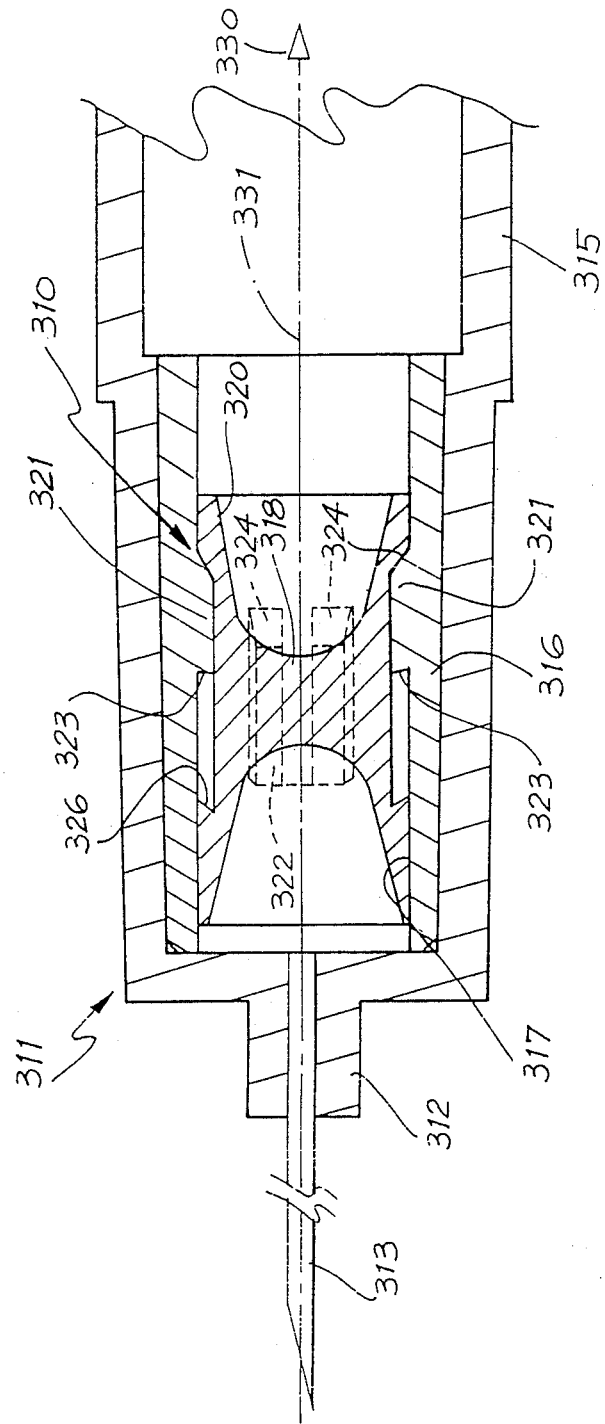
FIG. 15 is a schematic part sectioned side elevation of the valve assembly of FIG. 14, with the valve member in a second operative position.
Figure 16:
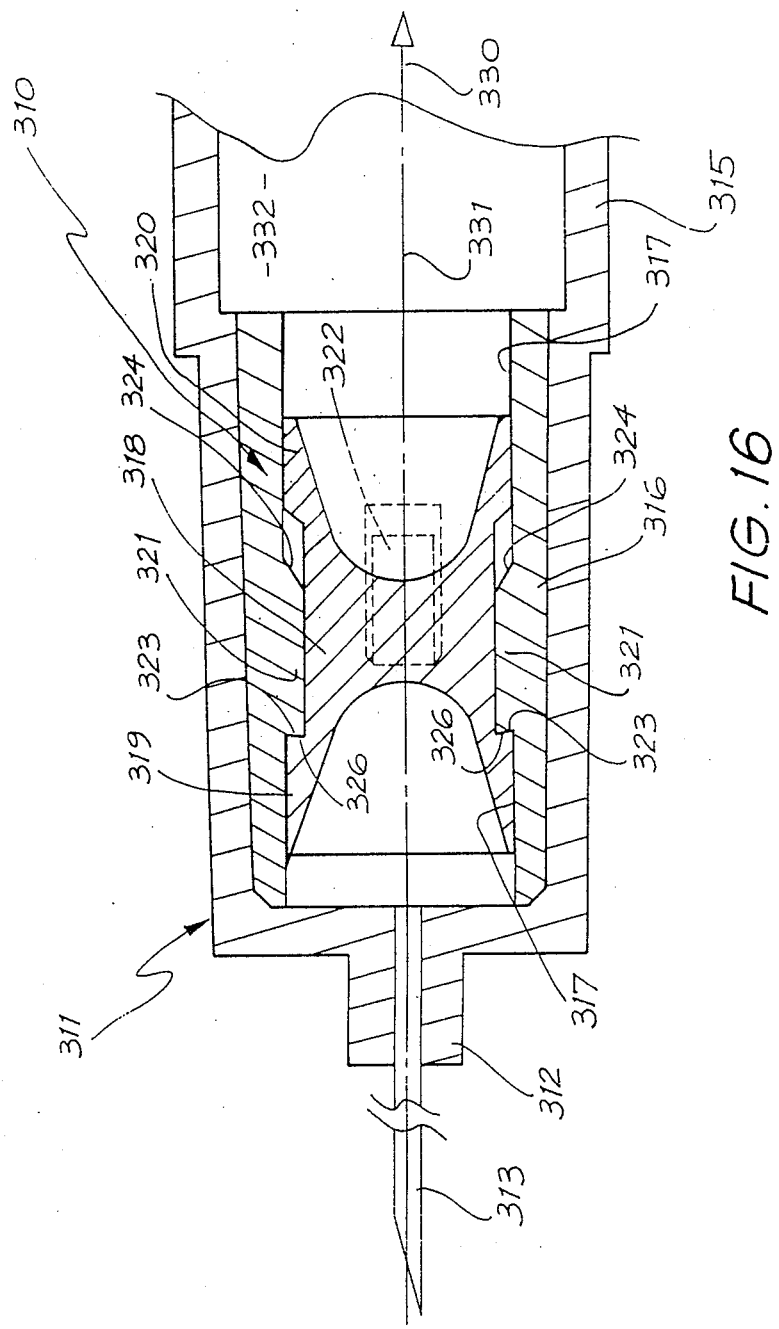
FIG. 16 is a schematic part sectioned side elevation of the valve assembly of FIG. 14, with the valve member in a third operative position.
Figure 17:
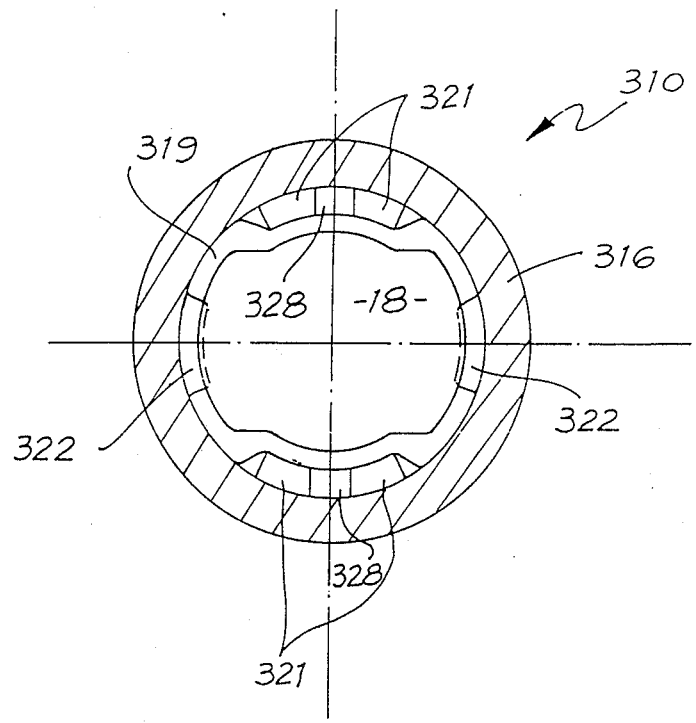
FIG. 17 is a schematic part sectioned end elevation of the valve assembly of FIG. 14 sectioned along the line 17—17.

Through the preferred embodiment shows the invention in the needle portion of a syringe other ways of carrying out the invention are also contemplated. For example, the valve means of the invention can be provided in the neck portion 5, the end portion of the main body portion 1, or in a needle portion 3 integral with the main body of a syringe. The valve means can also be provided as a separate module in any of the portions 3, 5 or 6, or as a module which is securely fixed at manufacture the neck portion 5 and the needle portion 3 of a syringe, as illustrated in FIG. 5. The main body portion 1, the valve means 7 and the needle portion 3 in the latter case thereby forming a single integral unit. Equally the valve means 7 can be fixed to the neck portion 5, or the needle portion 3 separately for cooperation with a needle portion 3 or a neck portion 5 respectively of a syringe.

When the valve means is used as a separate module within region 6 of the main body portion 1 of a syringe, it is to be understood that the module can be inserted as a plug, the size of which can be standardised and fitted to variously sized syringes by sleeves or other suitable fixing or securing means.

In any of the above situations there is a possibilitly that the syringe may be re-useable if the plunger portion 2 is withdrawn and the syringe filled from the rear. To prevent this situation the rear end of the main body portion 1 through which the plunger is inserted can be crimped or heat staked after the plunger has been inserted at manufacture.

Equally, stop means can be provided to prevent false operation of the valve means during transit.

In FIGS. 6 to 9 of the accompanying drawings there is schematically depicted a syringe 110 comprising an interacting cylinder 111 and piston 112 which co-operate to define a sealed chamber 113. The leading portion of the cylinder 112 is closed by a needle mounting 114 which receives a syringe needle 115.

Extending rearwardly from the piston 112 is a piston rod 116 extending to an end flange 117. The end of the cylinder 111 is provided with a pair of flanges 118 which are gripped by the user together with the flange 117. The piston 112 is provided with one or more sealing rings 119.

Located within the chamber 113 is a movable valve member 120 which is slidably received by the internal cylindrical surface of the cylinder 111, and divides the chamber 113 into two sub-chambers 121 and 122. The sub-chamber 121 being located adjacent the needle mounting 114, while the sub-chamber 122 is located between the piston 112 and the valve assembly 120.

The valve member 120 includes a main body 123 upon which there is mounted a pair of valve flaps 124 and 125 as well as a pair of pawl members 126.

The internal peripheral surface of the cylinder 111 is provided with shaped recesses 127 which slidably receive the valve flaps 125, and shaped recesses 128 which receive the pawl members 126.

The internal peripheral surface of the cylinder 111 is also provided with abutments 129 which are positioned to be engaged by the pawl members 126.

The valve member 120 is longitudinally slidably movable within the cylinder 111 so as to be movable between a first operative position as shown in FIG. 2, and a second operative position as shown in FIG. 3 In the operative position of FIG. 2, a user of the syringe can increase the volume of the chamber 113 by moving the piston away from the needle 113. A liquid is then drawn in through the needle into the chamber 113 and is allowed to pass between the sub-chambers 121 and 122 via inward deflection of the valve flap 125. The valve flap 125 deflects towards the longitudinal axis 30 of the cylinder 111. Once a desired amount of liquid has been drawn into the syringe 110, the needle 115 is inserted and the piston 112 moved towards the needle 115. As the pressure in the chamber 122 increases, the valve flap 125 is forced into sealing engagement with the internal peripheral surface of the cylinder 111. This pressure further causes movement of the valve member 120 towards the needle 115 until the body 123 abuts a step 131, as shown in FIG. 3. Further movement of the piston 112 then causes the liquid to move past the body 123 to cause inward deflection of the valve flap 124 towards the longitudinal axis 130.

In the position shown in FIG. 3 it should be appreciated that the body 123 is in sealing engagement with the internal peripheral surface of the cylinder 111 apart from the recess 127 which is selectively closed by the valve flap 124.

When the valve assembly 120 is in the position shown by FIG. 3, the pawl members 126 are located forward of the abutments 129. Accordingly, if an attempt is made to re-use the syringe by again moving the piston 112 away from the needle 115, the valve member will not return to the position as shown in FIG. 2. However, while in the position of FIG. 3, the valve flap 124 prohibits liquid being drawn into the chamber 113 and therefor the sub-chamber 122 is sealingly cut off from the sub-chamber 121.

It is desirable in some instances to ensure that the needle 25 has been correctly located by drawing into the syringe 110 a small amount of blood. This is done after the syringe has been filled with a liquid to be injected. To provide for this, the step 131 is located relative to the abutments 129 such that a small movement of the valve member 120 away from the needle 115 is possible until the pawl members 26 engage the abutments 129.

In FIGS. 210 and 211 of the accompanying drawings, there is schematically depicted a portion 210 of a syringe. The syringe includes a cylindrical wall 111 which sealingly slidably receives a piston which is not illustrated. One end of the chamber 212 is closed by the piston, while the other end of the chamber 212 is closed by a needle mounting. The chamber 212 is divided into two sub-chambers 213 and 214 by means of a valve member 215. The valve member 215 is formed of flexible resilient material and is provided with a first flexible end wall 216, and a second end wall 217.

The cylindrical wall 211 has an internal peripheral surface provided with an annular lip 218 and at least one longitudinally extending projection 219. The projections 219 extend longitudinally from this lip 218 towards the piston.

Located forward from the lip 218 towards the needle mounting, is at least one projection 220.

In operation of the syringe described with reference to FIGS. 1 and 2, initially the valve member 215 is located engaged by the projections 219 so that the end wall 217 is at least partly deformed, as best seen in FIG. 2. The piston is also located so that the chamber 212 has a minimum volume. Thereafter, a liquid to be injected is drawn into the syringe by the piston being moved away from the valve member 215 in the direction of the arrow 221. Once the desired amount of liquid is contained within the syringe, the needle is oriented vertically and air expelled from within the syringe. It should be appreciated that the vast majority of the liquid to be injected is located in the sub-chamber 214. The liquid is allowed to enter the sub-chamber 214 by passing around the deformed end wall 217 and causing deflection of the end wall 216.

Once the desired amount of liquid is located in the syringe, the needle is oriented vertically and air expelled from within the syringe. This operation will move the valve member 215 to a position located closer to the needle mounting. More particularly, the end wall 217 is moved from engagement with the projections 219, and abuts the projections 220. When in this position, the end wall 216 is engaged by the projections 219. It should be appreciated that this forward movement of the valve member 215 is caused by the pressure within the liquid, applied against the end wall 216.

Once the syringe needle has been inserted, and the piston moved to inject the liquid, the liquid moves past the deformed end wall 216 and around past the annular space existing between the internal peripheral wall of the cylinder 211 and the end wall 217. This deformation of the end wall 216 is caused by the engagement between the end wall 216 and the projections 219.

Further use of the syringe, by movement of the piston again in the direction of the arrow 221 is prevented by the valve member 215 being moved in the direction of the arrow 221 until the valve member sealingly engages the annular lip 218. Since insufficient force can be applied to the valve member 215 to cause deformation thereof by engagement with the projections 219, further use of the syringe is inhibited.

It should be appreciated that the projections 220 are spaced from the projections 219 so that a certain amount of movement of the valve member 215 is permitted until the end wall 217 sealingly contacts the lip 218. This enables the syringe needle to be inserted in a vein and the piston drawn back, a limited amount, to draw in a small quantity of blood to thereby detect whether the syringe needle has been correctly inserted.

Figure 4:
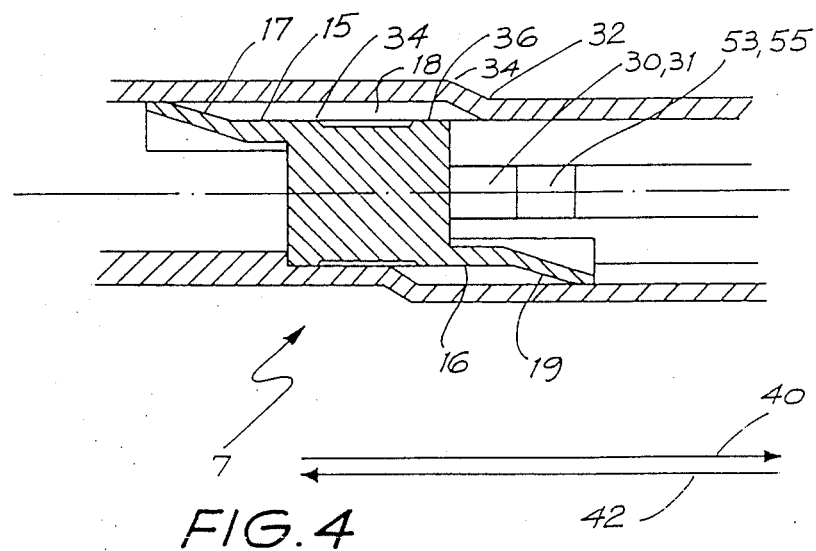
FIG. 4 is a schematic sectioned side elevation of the syringe portion of FIG. 2 in a second operative position.

In FIGS. 3 and 4 there is schematically depicted a portion 230 of a syringe. In this particular embodiment, the syringe has a cylindrical wall 231 encompassing a chamber 232. The chamber is closed at one end by means of a piston, while the other end is closed by a needle mounting.

The chamber 232 is divided into two sub-chambers 233 and 234 by means of a valve member 235. The valve member 235 is formed of flexible resilient material and has a pair of end walls 236 and 237. The end walls 236 and 237 are joined by a stem 238.

The internal peripheral surface of the wall 231 is provided with an annular lip 239 as well as at least one longitudinally extending projection 240.

In the position depicted in FIGS. 12 and 13, the end wall 217 is engaging the projections 240 so as to be deformed thereby.

Initially, the valve member 235 is located in the position depicted in FIG. 3. The piston is located so that the volume of the chamber 232 is minimized. To draw a liquid into the syringe, the piston is moved in the direction of the arrow 241 away from the valve member 235. The liquid is drawn into the sub-chamber 234 via movement of the liquid past the end wall 237, due to its deformation, and the deflection of the end wall 236 away from the cylindrical wall 231. Once the desired amount of liquid has been drawn into the syringe, the needle is oriented vertically and air expelled. Movement of the piston to achieve this, moves the valve member 235 to a position such that the end wall 237 is forward of the projections 240. However, the end wall 236 is engaged by the projections 240 and is deformed to enable liquid to pass thereby and between the end wall 237 and the internal peripheral surface of the cylindrical wall 231.

Once the needle has been inserted, the piston is moved so as to minimize the volume of the chamber 232 with the liquid again passing by the deformed end wall 236 and past the end wall 237.

Re-use of the syringe is inhibited since movement of the piston again in the direction 241 moves the valve member 235 to bring the end wall 237 back into sealing contact with the annular lip 239.

The valve member 235 is permitted a certain degree of movement before the end wall 237 is moved back into sealing contact with the annular lip 239, to enable the syringe to be inserted and a smaller amount of blood drawn into the syringe to indicate whether the needle has been correctly located.

In FIGS. 14 to 17 of the accompanying drawings there is schematically depicted a valve assembly 310 to be mounted within the end portion 311 of a syringe. The end portion 311 includes a needle mounting 312 to receive a syringe needle 313. The end portion 311 includes a generally cylindrical section 314, which if need be may be slightly tapered so as to be "frustoconical" in configuration. Extending from the cylindrical portion 314 is the main body 315 of the syringe which slidably sealingly receives the piston (not illustrated).

The cylindrical section 314 receives the valve assembly 310. The valve assembly 310 includes a valve sleeve 316 which has an outer peripheral surface sealingly mated with the internal peripheral surface of the cylindrical section 314. The internal peripheral surface 317 slidably receives a movable valve member 318. The valve member 318 is of a unitary construction, and is preferably moulded or formed from a resilient elastic material. The valve member 318 has a pair of annular sealing flanges 319 and 320 which provide sealing surfaces which slidably engage the surface 317.

The surface 317 is provided with two sets of projections 321 and 322, with the set of projections 321 being located closer to the needle than the second set of projections 322. The first set of projections 321 include two projections which are located on diametrically opposite sides of the surface 317, and are coextensive and parallel. The second set of projections 322 which are longitudinally spaced from the first set of projections 321 toward the rear of the syringe, also include a pair of projections, which are located on diametrically opposite sides of the surface 317, and are coextensive and parallel. The projections 322 are spaced 390 degrees angularly about the longitudinal axis 331, from the projections 321.

As best seen in FIGS. 1 and 3, each of the projections 321 and 322 has a leading face 323 which may be generally normal to the surface 317, or slightly inclined thereto so as to provide a barb which will engage the movable valve member 318. The rear end of each projection 321 and 322 is provided by a ramp surface 324.

The valve member 318 is provided with an annular recess 325 with a leading surface 326. The recess 325 has a rear surface 327. The surface 326 extends generally normal to the longitudinal axis 331, while the surface 327 is inclined to the axis 331 by an acute angle.

Each of the projections 321 is provided with a longitudinally extending passage 328 through which a liquid to be injected may pass.

In operation of the above described valve assembly 310, the movable valve member 318 begins in a starting position as seen in FIGS. 1 and 4. The projections 321 are engaged with the flange 319 so that the flange 319 is resiliently deformed so that portions thereof are spaced from the surface 317 so that the flange 319 is no longer in sealing contact with the surface 317. When the piston of the syringe is located adjacent the valve assembly 310 and moved in the direction of the arrow 330, a liquid is drawn in through the needle 313, pass the flange 319, and due to the pressure differential across the flange 320, the flange 320 deflects from a sealing contact with the surface 317, and permits the liquid to enter the main chamber 332 of the syringe. When the desired amount of liquid has been drawn into the syringe, and the operator wishes to expel any air contained in the syringe the needle 313 is placed so as to extend vertically. Thereafter, any air contained in the syringe will move upwardly. The operator then moves the piston or plunger to expel the air. When the piston moves, the pressure within the liquid within the chamber 331 causes the valve member 318 to move towards the needle 313, so that the flange 319 moves from operative contact with the projections 321. When this occurs, the flange 320 moves in contact with the projections 322. Accordingly, the flange 320 is moved from sealing contact with the surface 317 The liquid then is able to pass the flange 320 and cause deflection of the flange 320 to pass towards the needle 313. This position is shown in FIG. 2.

In some instances it is desirable to test to determine whether the needle has been correctly inserted This is achieved by drawing back on the piston and drawing into the syringe a small amount of blood. This test can be carried out due to the distance between the surface 326 and the surface 323, which distance, permits a small amount of rearward movement of valve member 318. When the piston is drawn back, the movable valve member 318 moves until the surface 326 engages the surfaces 323 of the projections 321. Once this has occurred, the movable valve member 318 is prevented from any further rearward movement. Once in this position, the flanges 319 are in sealing contact with the surface 317 and prevent any further material being drawn into the syringe. To inject the liquid contained within the chamber 332, again the piston is moved forward towards the needle 313 and past the flanges 320 (as they are deformed by the projections 322). The pressure in the liquid then deflects the flanges 319 away from the surface 317 so that the liquid can then reach the needles 313.

Re-use of the syringe is inhibited since once the syringe has been used, the surface 326 is located forward of the surfaces 323 of the projections 321. Once this has occurred, the valve member 318 prevents any liquid being drawn into the chamber 332.

We claim:
1. A single use syringe comprising;

an inter-acting piston and cylinder defining a variable volume chamber within which a liquid to be injected is drawn;

a needle mounting at one end of said cylinder, to receive a needle, a passage extending through said mounting enabling liquid communication between said cylinder and said needle;

a piston rod attached to said piston and operable by a user to cause movement of said piston to vary the volume of said chamber;

a valve means including a valve body located within said chamber between said mounting and said piston and dividing said chamber into a first sub-chamber located between said mounting and valve means, and a second sub-chamber located between said valve means and said piston, said valve body being movable longitudinally of said cylinder between a first position and a second position, and said valve means includes a first valve which, when said body is in said first position, permits flow from said first sub-chamber to said second sub-chamber and prevents flow from said second sub-chamber to said first sub-chamber, but when said body is in said second position, said first valve permits flow from said second sub-chamber to said first sub-chamber and prevents flow from said first sub-chamber to said second sub-chamber, and a second valve which, when said body is in said first position, permits flow from said first sub-chamber to said second sub-chamber, but prevents flow from said first sub-chamber to said second sub-chamber when said body is in said second position; and means to prevent movement of said body from said second position to said first position.

2. The syringe of claim 1, wherein said first position of said body is closer to said mounting than the second position of said body.

3. The syringe of claim 1 or 2 wherein said first and second valves include valve flaps attached to said body, and said cylinder has recesses selectively sealingly co-operating with said valve flaps.

4. The syringe of claim 2 further including first projection means to engage the valve flap of said first valve, which first projection means is positioned to deflect said valve flap from sealing engagement with said cylinder when said body is in said second position, and second projection means to engage thje valve flap of said second valve means to move it from sealing contact with said cylinder when said body is in said first position.

5. The syringe of claim 1 wherein said valve body is formed of resilient material, and said valves include resilient annular flanges on said body, and a first projection means on said cylinder and positioned to engage the flap of the first valve when said body is in said second position, and second projection means which engages the flange of said second valve when said body is in said first position.

6. A valve assembly for a syringe having an interacting piston and cylinder, with the cylinder terminating at one end with a mounting to receive a syringe needle, said piston and cylinder co-operating to define a variable volume working chamber which receives a liquid to be injected by the syringe, said valve assembly being adapted to be located within said chamber so as to divide said chamber into a first sub-chamber located adjacent the needle mounting, and a second sub-chamber located adjacent the piston, said valve assembly including;
- a valve sleeve to be sealingly received within said cylinder so as to be coaxial with respect thereto, said sleeve having an internal peripheral surface;
- a movable valve member received within said sleeve and sealingly co-operating therewith so that in use of the syringe the valve member selectively controls the direction of flow of liquid within the syringe, said valve member having a pair of axially spaced annular sealing surfaces which sealingly engage said sleeve, and which are resiliently deformable;
- a first set of sleeve projections extending inwardly of said sleeve to engage a first one of said sealing surfaces;
- a second set of sleeve projections extending inwardly of said sleeve to engage the other sealing surface, said second set of sleeve projections being spaced longitudinally of said first set of sleeve projections; and
- wherein said valve member is longitudinally movable between a first portion wherein the first annular sealing surface is engaged with the first set of sleeve projections so as to be deformed and deflected from said sleeve so that liquid may pass thereby, and the other sealing surface is in sealing contact with said sleeve and inhibits the direction of fluid flow in a first direction, and a second position wherein said second sealing surface is engaged with said second set of sleeve projections so that liquid may pass thereby, and said first sealing surface is sealingly engaged with said sleeve to inhibit fluid flow in a second direction, which is opposite to said first direction.

7. A single use syringe having an interacting piston and cylinder, with the cylinder terminating at one end with a mounting to receive a syringe needle, said piston and cylinder cooperating to define a variable volume working chamber which receives a liquid to be injected by the syringe, and the valve assembly of claim 6, which valve assembly is located within said chamber so as to divide said chamber into said first sub-chamber and said second sub-chamber.

* * * * *